(12) United States Patent
Tateishi et al.

(10) Patent No.: US 8,569,058 B2
(45) Date of Patent: Oct. 29, 2013

(54) NERVE REGENERATION PROMOTERS

(75) Inventors: Narito Tateishi, Mishima-gun (JP); Junki Yamamoto, Mishima-gun (JP); Soichi Kawaharada, Mishima-gun (JP); Tsutomu Akiyama, Mishima-gun (JP); Masamitsu Hoshikawa, Mishima-gun (JP)

(73) Assignee: ONO Pharmaceutical Co., Ltd., Osaka (JP)

( * ) Notice: Subject to any disclaimer, the term of this patent is extended or adjusted under 35 U.S.C. 154(b) by 1533 days.

(21) Appl. No.: 10/574,479

(22) PCT Filed: Oct. 1, 2004

(86) PCT No.: PCT/JP2004/014879
§ 371 (c)(1),
(2), (4) Date: Oct. 5, 2006

(87) PCT Pub. No.: WO2005/032535
PCT Pub. Date: Apr. 14, 2005

(65) Prior Publication Data
US 2007/0043114 A1 Feb. 22, 2007

(30) Foreign Application Priority Data

Oct. 3, 2003 (JP) .............................. P. 2003-345123
Jun. 1, 2004 (JP) .............................. P. 2004-162909

(51) Int. Cl.
*C12N 5/00* (2006.01)
*C12N 5/02* (2006.01)

(52) U.S. Cl.
USPC .......................................... 435/377; 435/375

(58) Field of Classification Search
None
See application file for complete search history.

(56) References Cited

U.S. PATENT DOCUMENTS 4,431,833 A * 2/1984 Lodhi et al. ...................... 560/2
6,201,021 B1 * 3/2001 Ohuchida et al. ............. 514/558

FOREIGN PATENT DOCUMENTS

| JP | 7-316092 A | 12/1995 |
| JP | 9-238685 A | 9/1997 |
| JP | 9-263543 A | 10/1997 |
| JP | 2002-97158 A | 4/2002 |
| JP | 2002-308779 A | 10/2002 |
| WO | 01/39779 A1 | 6/2001 |
| WO | 02/102989 A2 | 12/2002 |

OTHER PUBLICATIONS

Mazo, Ellen "Stroke victims put big hopes in nerve cell transplants" Pittsburgh Post-Gazette, Apr. 12, 2000, pp. 1-3.*
Tateishi et al. (2002) Astrocytic activation and delayed infarct expansion after permanent focal ischemia in rats. Part II: Suppression of astrocytic activation by a novel agent ()-(−)-2-propyloctanoic acid (ONO-2506) leads to mitigation of delayed infarct expansion and early improvement. J. Cerebral Blood Flow & Metabolism 22: 723-734.*
Supplementary European Search Report dated Dec. 4, 2008.
Cui et al., "Valproic acid enhances axonal regeneration and recovery of motor function after sciatic nerve axotomy in adult rats," Brain Research, vol. 975, No. 1-2 (XP002504713), 2003, pp. 229-236.
Fiona Doetsch, et al., "Subventricular Zone Astrocytes Are Neural Stem Cells in the Adult Mammalian Brain", Cell, Jun. 11, 1999, pp. 703-716, vol. 97.
European Office Action issued Jul. 22, 2010, in the corresponding European patent application No. 04792173.9.

* cited by examiner

*Primary Examiner* — Anne-Marie Falk
(74) *Attorney, Agent, or Firm* — Sughrue Mion, PLLC

(57) ABSTRACT

A nerve regeneration which comprises a compound is represented by formula (I):

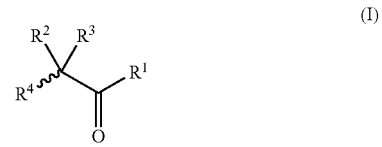

(wherein all symbols are shown in the description), a salt thereof or a prodrug thereof. The compound of the present invention is suppresses nerve cell death as a substance for accelerating growth and/or differentiation of stem cells (nerve stem cells, embryonic stem cells, bone marrow cells, etc.), a substance for accelerating growth and/or differentiation of nerve precursor cells, a potentiator for neurotrophic factor activity, a neurotrophic factor-like substance or a neurodegenerative suppressor, and accelerates repair and regeneration of nerve tissues by neogenesis, regeneration and/or axon evolution. In addition, the compound of the present invention is useful for preparation from brain tissues, bone marrow and/or embryonic stem cells of cells for transplant (nerve stem cells, nerve precursor cells, nerve cells, etc.) and also accelerates grafting, growth, differentiation and/or function expression of cells for transplant whereupon it is useful for prevention and/or treatment of neurodegenerative diseases.

2 Claims, 2 Drawing Sheets

IMMUNOSTAINED PICTURES (ANTI-βIII-TUBULIN ANTIBODY POSITIVE)

NO COMPOUND-ADDED GROUP    COMPOUND-ADDED GROUP

NERVE REGENERATION PROMOTERS

TECHNICAL FIELD

The present invention relates to a nerve regeneration accelerator useful as a medicament.

BACKGROUND ART

Since old days, it has been believed that nerve cells are not regenerated. However, since culturing of nerve stem cells in undifferentiated conditions have succeeded in about 1990, it has become clear that there are stem cells capable of differentiating into nerve cells even in adult brain and that nerve can be regenerated.

Nerve stem cells are cells which have a self-replicating ability and also have multipotency capable of producing nerve cells (neurons) and supporting cells such as astrocytes and oligodendrocytes. Usually, nerve cells are formed from undifferentiated nerve stem cells via nerve precursor cells. It has been also known that embryonic stem cells (ES cells), bone marrow cells (myeloid stem cells, etc.) and the like are capable of differentiating into nerve cells. At present, in the art which is ahead of the times such as in the art for regeneration of bone and skin tissues, it is possible to achieve an object to some extent by reappearance of the physical conditions inherent to the tissues. However, in order to use nerve regeneration as a medical art, it is not sufficient that nerve cells are just physically formed but how to mature and how to function the nerve cell is an important problem.

Neurodegenerative diseases such as Alzheimer's disease, Parkinson's disease, amyotrophic lateral sclerosis (ALS) and Huntington's disease are diseases which occur when nerve cell death takes place in a progressive manner. With regard to a method for treating such neurodegenerative diseases, a supplementary treatment in which deficiency of neurotransmitter is supplemented or a symptomatic treatment has been mostly carried out at present. However, in the supplementary treatment or the symptomatic treatment, progress of degeneration of the nerve cannot be completely suppressed but symptom proceeds. It has been known however that, even in such diseases, endogenous nerve stem cells existing in adult brain are differentiated into nerve cells. For example, it has been reported that, in ischemic model animals, nerve regeneration takes place from nerve stem cells (*J. Neurosci.*, 18, 7768-7778 (1998)).

In recent years, as an object of treatment of those neurodegenerative diseases, attempts for activating the inherent nerve stem cells and regenerating the disordered nerve tissue and function have been conducted (*Nature Medicine*, 4, 1313-1317 (1998); *Nature Medicine*, 6, 271-277 (2000)). Attempts where nerve stem cells are prepared from embryonic stem cells and aborted human brain or also from tissues of a patient per se and nerve regeneration is aimed by means of transplant have been conducted as well (*Nature*, 405, 951-955 (2000); *Eur. J. Neurosci.*, 10, 2026-2036 (1998)). In addition, an effect for improving the symptoms by administration of stem cells from peripheral blood vessel has been shown not only in neurodegenerative diseases but also in demyelinated diseases (*Nature*, 422, 688-694 (2003)).

In the meanwhile, it has been reported that 2-propylpentanoic acid derivatives have an action for improving the function of astrocytes and accordingly that they are useful as treating agent and/or preventive agent for neurodegenerative diseases, neural dysfunction after cerebrospinal wound and cerebral stroke, brain tumor, cerebrospinal diseases accompanied by infectious diseases, and the like (e.g., EP-A-0632008).

Such 2-propylpentanoic acid derivatives have been also reported to be useful as a treating agent and/or a preventive agent for Parkinson's disease or Parkinson's syndrome (e.g., EP-A-1174131).

Furthermore, actions as such of the 2-propylpentanoic acid derivatives have been reported to be due to an action for improving the function of abnormally activated astrocytes causes by action of decreasing of intracellular $S100\beta$ content (e.g., Tateishi, N. and eight others, *Journal of Cerebral Blood Flow & Metabolism*, 22, 723-734 (2002)).

It has been also reported that, in mature rat where axon of sciatic nerve is cut, the axon is elongated and kinetic function is recovered when 2-propylpentanoic acid is administered (e.g., Xia Zhang and six others, *Brian Research*, 975, 229-236 (2003)).

In those literatures, however, there is no description that 2-propylpentanoic acid derivatives accelerate growth and differentiation of nerve stem cells and nerve precursor cells and there is no reference that they have an action of inducing nerve cells from non-nervous cells such as glia cells. Furthermore, there has been neither description nor suggestion at all for a method where 2-propylpentanoic acid derivatives are used for cell preparation of nerve cells for transplant.

In spite of the fact that neurodegenerative diseases represented by Alzheimer's disease and Parkinson's disease are serious diseases resulting in deficiency of nerve, an effective method for the treatment of the diseases which is not a symptomatic one has not been found yet. For example, if only cutting of axon takes place in neurodegenerative disease as shown in animal models mentioned in the above document (Xia Zhang and six others, *Brian Research*, 975, 229-236 (2003)), there is a possibility that administration of 2-propylpentanoic acid can be used as an effective treating method. However, neurodegenerative disease is a general name for diseases in which not only axon but nerve cell itself gradually dies and no specific method for treating it has been found yet. In addition, no art has been found yet for inducing transplanted stem cells or endogenous stem cells to actually functioning nerve cells in stem cell transplant or in activation of endogenous stem cells which may be used as an effective treating method for neurodegenerative diseases in near future.

In view of the problems in the treatment of neurodegenerative diseases as such, there has been a brisk demand in the actual medical fields at present for the development of compounds which are useful as medicaments such as preventive agents and treating agents for neurodegenerative diseases.

DISCLOSURE OF THE INVENTION

When causes for neurodegenerative diseases and property of nerve cells themselves are taken into consideration, compounds having (1) neurotrophic factor-like action, (2) action for potentiating the activity of neurotrophic factor, (3) action of nerve cell neogenesis after nerve degeneration and (4) accelerating action for regeneration of nerve cell after nerve degeneration (e.g., (a) compounds which accelerate neogenesis, growth and differentiation of nerve stem cells and nerve precursor cells, (b) compounds which accelerate grafting, differentiation and growth of transplant cells when nerve stem cells, nerve precursor cells or nerve cells are transplanted or (3) compounds which accelerate maturation of nerve cells, etc.) are presumed to be useful. It is believed that compounds which fulfill those requirements suppress nerve cell death in neurodegenerative diseases and accelerate nerve regeneration of endogenous or transplant cells even after nerve cell death happens and accordingly that symptom of the disease is improved. Thus, the present inventors have carried out intensive investigations for finding the compounds which fulfill the above requirements and, as a result, they have found that the fatty acid compound according to the present invention or a salt thereof or a prodrug thereof (hereinafter sometimes referred to the compound of the present invention) is an excellent compound fulfilling the requirements whereupon the present invention has been achieved.

The present inventors have further carried out intensive investigations for a accelerating action for nerve regeneration by the compound of the present invention and found that the compound of the present invention has not only an action of accelerating growth and differentiation of stem cells and nerve precursor cells but also an actually wonderful action of accelerating the differentiation from glia cells such as astrocytes to nerve cells whereupon the present invention has been achieved. Incidentally, in the above-mentioned Patent Document (EP-A-0632008), there is a description that 2-propylpentanoic acid derivative compound has an action of improving the astrocyte function and inhibits the induction of astrocyte to reactive astrocyte but there is neither description nor suggestion at all that the compound has an action of inducing the differentiation of astrocyte to nerve cell whereupon the present invention is quite unobvious from the above-mentioned Patent Document.

Thu, the present invention relates to the followings:

1. A nerve regeneration accelerator, which comprises a fatty acid compound excluding retinoic acid and a prostaglandin compound, a salt thereof or a prodrug thereof.
2. The nerve regeneration accelerator according to the above 1, wherein the fatty acid compound is an unsaturated fatty acid compound.
3. The nerve regeneration accelerator according to the above 1, wherein the fatty acid compound is a saturated fatty acid compound.
4. The nerve regeneration accelerator according to the above 1, wherein the fatty acid compound is a branched chain fatty acid compound.
5. The nerve regeneration accelerator according to the above 1, wherein the fatty acid compound is a linear or branched chain fatty acid compound having from 4 to 20 carbon atoms.
6. The nerve regeneration accelerator according to the above 1, wherein the fatty acid compound is represented by formula (I):

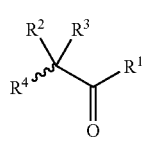

wherein $R^1$ represents hydroxyl; $R^2$ and $R^3$ each independently represents (a) hydrogen, (b) chlorine, (c) C3-10 alkyl, (d) C3-10 alkenyl, (e) C2-10 alkoxy, (f) C2-10 alkylthio, (g) C3-7 cycloalkyl, (h) phenyl, (i) phenoxy, (j) (C2-10 alkyl substituted with one or two chorine atom(s)) —$CH_2$—, (k) (C1-5 alkyl substituted with one or two substituent(s) selected from C1-4 alkoxy, C3-7 cycloalkyl, phenyl and phenoxy)-$CH_2$—, (l) (C1-10 alkyl in which one carbon atom is substituted with 1 to 3 fluorine atom(s)) —$CH_2$—, or (m) oxidized C3-10 alkyl, or $R^2$ and $R^3$ are taken together to represent C3-10 alkylidene; and $R^4$ represents C2-3 alkyl or oxidized C2-3 alkyl.

7. The nerve regeneration accelerator according to the above 6, wherein the fatty acid compound is (1) 2-propyloctanoic acid, (2) (2R)-2-propyloctanoic acid, (3) (2S)-2-propyloctanoic acid, (4) 2-propylpentanoic acid, (5) (2R)-7-oxo-2-propyloctanoic acid, (6) (2R,7R)-7-hydroxyl-2-propyloctanoic acid, (7) (2R,7S)-7-hydroxyl-2-propyloctanoic acid, or (8) (2R)-8-hydroxyl-2-propyloctanoic acid.
8. The nerve regeneration accelerator according to the above 7, wherein the fatty acid compound is (2R)-2-propyloctanoic acid.
9. The nerve regeneration accelerator according to any one of the above 1 to 8, which is a nerve tissue regenerator or a neural function regenerator.
10. The nerve regeneration accelerator according to any one of the above 1 to 8, which is an accelerating agent for grafting, differentiating, proliferating and/or maturing a stem cell, a nerve precursor cell or a nerve cell.
11. The nerve regeneration accelerator according to the above 10, wherein the stem cell is an embryonic stem cell, a myeloid stem cell or a nerve stem cell.
12. The nerve regeneration accelerator according to the above 10, wherein the stem cell, the nerve precursor cell or the nerve cell is an endogenous cell.
13. The nerve regeneration accelerator according to the above 10, wherein the stem cell, the nerve precursor cell or the nerve cell is a transplant cell.
14. The nerve regeneration accelerator according to any one of the above 1 to 8, which induces a nerve cell from a mesenchymal cell, a bone marrow stromal cell or a glia cell.
15. The nerve regeneration accelerator according to the above 14, wherein the glia cell is an astrocyte.
16. The nerve regeneration accelerator according to any one of the above 1 to 8, wherein the nerve is a central nerve or a peripheral nerve.
17. The nerve regeneration accelerator according to the above 16, wherein the central nerve is a cerebral nerve, a spinal nerve or an optic nerve.
18. The nerve regeneration accelerator according to the above 16, wherein the peripheral nerve is a motor nerve or a sensory nerve.
19. The nerve regeneration accelerator according to any one of the above 1 to 8, which is used for culture of a nerve stem cell for transplant, a nerve precursor cell for transplant or a nerve cell for transplant.
20. The nerve regeneration accelerator according to any one of the above 1 to 8, which is a neurotrophic factor-like agent.
21. A method for accelerating nerve regeneration in a mammal, which comprises administering to a mammal an effective amount of the compound described in any one of the above 1 to 8, a salt thereof or a prodrug thereof.
22. A method for culturing a cell for transplant, which comprises adding an effective amount of the compound described in any one of the above 1 to 8, a salt thereof or a prodrug thereof to a medium comprising a nerve stem cell for transplant, a nerve precursor cell for transplant or a nerve cell for transplant.
23. Use of the compound described in any one of the above 1 to 8, a salt thereof or a prodrug thereof for the manufacture of a nerve regeneration agent.
24. Use of the compound described in any one of the above 1 to 8, a salt thereof or a prodrug thereof for the manufacture of an additive agent for culture of a nerve stem cell for transplant, a nerve precursor cell for transplant or a nerve cell for transplant.

25. A medicament which comprises a combination of the compound described in any one of the above 1 to 8, a salt thereof or a prodrug thereof with at least one selected from an acetylcholine esterase inhibitor, a nicotinic receptor regulator, a β secretase inhibitor, a γ secretase inhibitor, a β amyloid protein aggregation inhibitor, a β amyloid vaccine, a β amyloid protease, a brain function activator, a dopamine receptor agonist, a monoamine oxidase inhibitor, an anticholinergic drug, a catechol-O-methyltransferase inhibitor, a drug for treating amyotrophic lateral sclerosis, a drug for treating hyperlipidemia, a drug for treating abnormal behavior and/or poriomania accompanied with progress of dementia, an apoptosis inhibitor, a drug for accelerating nerve differentiation and/or regeneration, an antihypertensive drug, a drug for treating diabetes, an antidepressant drug, an antianxiety drug, a nonsteroidal anti-inflammatory drug, a disease modifying antirheumatic drug, a TNF inhibitor, a MAP kinase inhibitor, a steroid drug, a sex hormone derivative, parathyroid hormone and a calcium acceptor antagonist.

26. A process for preparation of cells for transplant, which comprises adding an effective amount of the compound described in any of the above 1 to 8, a salt thereof or a prodrug thereof to a medium comprising nerve stem cells for transplant, nerve precursor cells for transplant or nerve cells for transplant.

27. A process for preparation of cells for transplant, which comprises adding an effective amount of the compound described in any of the above 1 to 8, a salt thereof or a prodrug thereof to a medium comprising nerve stem cells for transplant, nerve precursor cells for transplant or nerve cells for transplant.

"Nerve regeneration" used in the present invention includes both "nerve neogenesis" and "nerve regeneration" which are the terms used in the relevant art. Thus, when nerve cells and/or mature nerve cells in the living body or medium increase in case the compound of the present invention is administered to the living body or added to the medium for cell culture, all of them are included in nerve regeneration used in the present invention.

In the present invention, nerve regeneration may be classified into qualitative nerve regeneration and quantitative nerve regeneration. The quantitative nerve regeneration means increase of the numbers of nerve cells, and the qualitative nerve regeneration means increase of mature nerve cells. Here, the mature nerve cells mean nerve cells which are matured or, in other words, nerve cells which have grown up to a state where functional action such as sending and receiving of signals is possible. The nerve regeneration as such may take place either in vivo or in vitro and, particularly with regard to nerve regeneration in vivo, quantitative nerve regeneration in vivo and qualitative regeneration in vivo may be called, for example, "nerve tissue regeneration" and "nerve function regeneration", respectively.

In the present invention, the nerve regeneration also includes a meaning that process of normal development in nerve is reappeared at least partially in addition to a meaning of the above-mentioned increase in nerve cells and/or mature nerve cells. Thus, when any of the processes of grafting, differentiation, growth and/or maturation of cells which finally become nerve cells or mature nerve cell or are known to become so (hereinafter, referred to as cells for regeneration) is induced, all of them are included in nerve regeneration according to the present invention. It goes without saying that the process as such may take place either in vivo or in vitro.

In the present invention, the nerve regeneration is not limited to the type and the source of the cells for regeneration. Examples of the cells for regeneration include stem cells (such as nerve stem cells, embryonic stem cells and bone marrow cells), nerve precursor cells and nerve cells. Those cells may be cells to be endogenous or exogenous (e.g., transplant cells). As the exogenous cells, it is also possible to use mature nerve cells. The exogenous cells may be either autologous cells or heterologous cells. Furthermore, even in the case of the cells which are more undifferentiated than nerve stem cells, all of them are included in the nerve regeneration according to the present invention, so long as they are differentiated via nerve stem cells. Furthermore, even in the case of cells where differentiation step proceeded from nerve stem cells in direction other than nerve cells (for example, glia cells (e.g., astrocytes, oligodendrocyte, microglia, ependymal cells, etc.), glia precursor cells, and the like), all of them are included in the nerve regeneration according to the present invention, so long as they are differentiated into nerve cells and/or mature nerve cells.

In the present invention, the nerve regeneration may be on the basis of any mechanism. For example, it may be one the basis of neurotrophic factor-like action or potentiating action for neurotrophic factor activity. Here, the neurotrophic factor means, for example, factors which act as nutrition to nerve stem cells, nerve precursor cells, nerve cells, mature nerve cells and the like. With regard to the neurotrophic factor, proteins such as NGF (nerve growth factor), BDNF (brain derived neurotrophic factor) and insulin-like growth factor have been already known. The neurotrophic factor-like action may be an action of those neurotrophic factors and examples include elongating action of axon, synthesis accelerating action for neurotransmitter, accelerating action for differentiation and growth of nerve cells, action as nutrients for maintaining the activity of nerve cells, synapse-forming action and nerve cell protecting action although they are non-limitative. The potentiating action for neurotrophic factor activity means the activity which potentiates the action by the above neurotrophic factor.

Nerve stem cells, nerve precursor cells, nerve cells and the like for transplant which are present in the living body or are taken out outside the living body can be grown and/or differentiated into cells which are much more differentiated. To be more specific, the nerve stem cells can be grown and/or differentiated into nerve precursor cells, nerve cells, mature nerve cells, functional nerve cells and the like; the nerve precursor cells can be grown and/or differentiated into nerve cells, mature nerve cells, functional nerve cells and the like; and nerve cells can be grown and/or differentiated into mature nerve cells, functional nerve cells and the like. Although a method for identifying those cells may be carried out by a known method, it is preferred, for example, that detection is conducted using protein, mRNA and the like which are characteristically expressed by those cells for each differentiating stage as an indexes. With regard to such indexes, nestin and the like may be used for nerve stem cells; PSA-NCAM, doublecortin and the like may be used for nerve precursor cells; βIII-tubulin (Tuj 1) and the like may be used from nerve cells; MAP 2, NeuN, NSE and the like may be used for mature nerve cells; and GABA and the like may be used for functional nerve cells. Incidentally, in the present specification, the nerve cells and a part of the nerve precursor cells may be called immature nerve cells with a sense of non-mature nerve cells.

A method of culturing the cells for transplant in the present invention is characterized in adding the compound of the present invention to a medium and, therefore, known art may be used for culturing conditions such as a fundamental medium and other additives. With regard to specific culturing conditions, methods which will be mentioned in Examples are exemplified.

With regard to a method for culturing the cells for transplant in the present invention, that in which the compound of the present invention contacts to the cells for transplant in any of steps during the culturing period may be used and is not limited according to the fact whether the contacting time is short or long.

The method for culturing the cells for transplant in the present invention can also provide excellent effects by combining with other known art. For example, a method where electric stimulation and other physical or chemical stimulation and the like are applied to embryonic stem cells and the like to prepare a lot of nerve stem cells has been known and it is possible that the compound of the present invention is administered to a patient after transplanting the nerve stem cells prepared by such a method, that the compound of the present invention is added into the brain together with the transplant or that the compound of the present invention is added as an additive in the culturing during, before or after the stimulation.

In the present invention, the fatty acid compound can be not be limited, so long as it is an aliphatic compound having one carboxyl group. Here, the aliphatic compound means a compound in which a carbon atom to which a carboxyl group is bound is a constituting atom for the carbon chain. The carbon chain in the fatty acid compound may be either saturated or unsaturated and may be either linear or branched. The fatty acid compound having such a carbon chain may be referred to as a saturated fatty acid compound, an unsaturated fatty acid compound, a linear fatty acid compound and a branched chain fatty acid compound, respectively.

In the present invention, the prostaglandin compound is monocarboxylic acid having 20 carbon atoms and is a compound having the following basic skeleton.

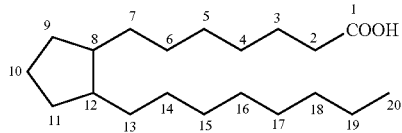 [SMILES: CCCCCCCCC1CCCC1CCCCCCC(=O)O]

In the present invention, the C1-4 alkoxy means, for example, methoxy, ethoxy, propoxy, butoxy, isomeric groups thereof, and the like.

In the present invention, the C1-4 alkyl means, for example, methyl, ethyl, propyl, butyl, isomeric groups thereof, and the like.

In the present invention, the 4- to 7-membered heterocycle containing one nitrogen atom means, for example, pyrrole, pyridine, azepine, a partially saturated or a fully saturated ring thereof (e.g., pyrrolidone, piperidine, etc.), and the like.

In the present invention, the 4- to 7-membered saturated heterocycle containing one or two nitrogen atom(s) together with a nitrogen bound thereto means, for example, azetidine, pyrrolidine, piperidine, perhydroazepine, pyrazolidine, imidazolidine, perhydrodiazine (e.g., piperazine, etc.), perhydrodiazepine and the like.

In the present invention, the 4- to 7-membered saturated heterocycle containing one nitrogen atom and one oxygen atom together with a nitrogen atom bound thereto means, for example, oxazolidine, perhydrooxazine (e.g., morpholine, etc.), perhydrooxazepine and the like.

In the present invention, the amino acid residue which is represented together with a nitrogen atom bound thereto may be any amino acid residue, and the residue includes one in which a carboxyl group is converted to ester. Specific examples thereof include glycine, alanine, serine, cysteine, cystine, threonine, valine, methionine, leucine, isoleucine, norleucine, phenylalanine, tyrosine, tyronine, proline, hydroxyproline, tryptophan, aspartic acid, glutamic acid, arginine, lysine, ornithine, histidine residues, esters thereof (e.g., C1-4 alkyl esters, benzyl ester, etc.), and the like.

In the present invention, the C1-10 alkyl in which one carbon atom is substituted with one to three fluorine atom(s) means, for example, groups in which one carbon atom in methyl, ethyl, propyl, butyl, pentyl, hexyl, heptyl, octyl, nonyl, decyl, isomeric groups thereof, and the like is substituted with one, two or three fluorine atom(s).

In the present invention, the C3-10 alkyl means, for example, propyl, butyl, pentyl, hexyl, heptyl, octyl, nonyl, decyl, isomeric groups thereof, and the like.

In the present invention, the C3-10 alkenyl means, for example, propenyl, butenyl, pentenyl, hexenyl, heptenyl, octenyl, nonenyl, decenyl, isomeric groups thereof, and the like.

In the present invention, the C2-10 alkoxy means, for example, ethoxy, propoxy, butoxy, pentyloxy, hexyloxy, heptyloxy, octyloxy, nonyloxy, decyloxy, isomeric groups thereof, and the like.

In the present invention, the C2-10 alkylthio means, for example, ethylthio, propylthio, butylthio, pentylthio, hexylthio, heptylthio, octylthio, nonylthio, decylthio, isomeric groups thereof, and the like.

In the present invention, the C3-7 cycloalkyl means, for example, cyclopropyl, cyclobutyl, cyclopentyl, cyclohexyl, cycloheptyl and the like.

In the present invention, the C2-10 alkyl means, for example, ethyl, propyl, butyl, pentyl, hexyl, heptyl, octyl, nonyl, decyl, isomeric groups thereof, and the like.

In the present invention, the C2-3 alkyl means, for example, ethyl, propyl and isopropyl.

In the present invention, the term "oxidized" in the oxidized C2-3 alkyl or the oxidized C3-10 alkyl means that the alkyl is substituted with one to three hydroxyl group(s) or oxo group(s). The oxy group and the hydroxyl group herein may be substituted at the same carbon atom only in the case of the terminal carbon atom of the alkyl.

In the present invention, the C1-5 alkyl means, for example, methyl, ethyl, propyl, butyl, pentyl, isomeric groups thereof, and the like.

In the present invention, the C3-10 alkylidene means, for example, propylidene, butylidene, pentylidene, hexylidene, heptylidene, octylidene, nonylidene, decylidene, isomeric groups thereof, and the like.

In the present invention, all isomers are included, unless otherwise indicated. For example, alkyl, alkenyl, alkynyl, alkoxy, alkylthio, alkylene, alkenylene and alkynylene include both linear and branched-chain ones. Moreover, all of isomers for double bond, ring and fused ring (E, Z, cis and trans forms), isomers due to the presence of an asymmetric carbon or the like. (R and S forms, α and β configurations, enantiomer and diastereomer), optically active substances having optical rotary power (D, L, d and l-forms), polar substances as a result of chromatographic separation (highly polar substance and lowly polar substance), equilibrated compounds, rotational isomers, a mixture thereof in any ratio and a racemic mixture are included in the present invention.

In the present invention; a symbol ⋰ means a bond to the opposite side (i.e., α-configuration); a symbol ⁄ means a bond to this side (i.e., β-configuration); a symbol ⋰ means an α-configuration, a β-configuration or a mixture thereof; and a symbol ⁄ means a mixture of an α-configuration and a β-configuration as is apparent for the skilled person in the art, unless otherwise indicated.

The salt of the compound of the present invention includes all salts which are pharmaceutically acceptable. Non-toxic and water-soluble salts are preferred as the pharmaceutically acceptable salts. Suitable salts, for example, include salts of alkali metals (e.g. potassium, sodium, lithium, etc.), salts of alkaline earth metals (e.g. calcium, magnesium, etc.), ammonium salts (e.g. tetramethylammonium salt, tetramethylammonium salt, etc.), salts of organic amines (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid addition salts (e.g., salts of inorganic acids (such as hydrochloride, hydrobromide, hydroiodide, sulfate, phosphate and nitrate), salts of organic acids (such as acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate and gluconate), etc.), and the like. The salts of the compounds of the present invention include solvates and solvates of the above-described salts of alkali metals, salts of alkaline earth metals, ammonium salts, organic amine salts and acid addition salts. The solvates are preferably non-toxic and water-soluble ones. Suitable solvates, for example, include solvates of water, alcohol solvents (e.g., ethanol, etc.), and the like. The compounds of the present invention can be converted into pharmaceutically acceptable salts by conventional methods.

A prodrug of the compound of the present invention or a salt thereof means a compound which is converted to the compound of the present invention or a salt thereof by reaction with an enzyme, gastric acid or the like in the living body or in cells of cultured cells. For example, with regard to a prodrug of the compound represented by formula (I) or a salt thereof, compounds in which $R^1$ is [1] C1-4 alkoxy, [2] C1-4 alkoxy substituted by one phenyl or [3] $NR^5R^6$ (wherein $R^5$ and $R^6$ each independently represents (1) hydrogen, (2) C1-4 alkyl, (3) phenyl, (4) phenyl substituted by (i) C1-4 alkoxy or (ii) carboxyl, (5) 4- to 7-membered heterocycle containing one nitrogen atom, (6) C1-4 alkyl substituted by (i) phenyl, (ii) phenyl substituted by C1-4 alkoxy or carboxyl or (iii) 4- to 7-membered heterocycle containing one nitrogen atom, (7) 4- to 7-membered saturated heterocycle containing one or two nitrogen atom(s) together with a nitrogen atom bound thereto, (8) 4- to 7-membered saturated heterocycle containing one nitrogen atom and one oxygen atom together with a nitrogen atom bound thereto or (9) an amino acid residue together with a nitrogen tom bound thereto) may be exemplified. Examples which are other than the above ones include that, when the compound of the present invention or a salt has an amino group, compounds in which the amino group is, for example, acylated, alkylated or phosphorylated (e.g., compounds in which the amino group of the compound represented by formula (I) or a salt thereof is eicosanoylated, alanylated, pentylaminocarbonylated, (5-methyl-2-oxo-1,3-dioxolen-4-yl) methoxycarbonylated, tetrahydrofuranylated, pyrrolidylmethylated, pivaloyloxymethylated, acetoxymethylated, tert-butylated, etc.); that, when the compound of the present invention or a salt thereof has a hydroxyl group, compounds where the hydroxyl group is, for example, acylated, alkylated, phosphorylated or borated (e.g., compounds in which the hydroxyl group of the compound represented by formula (I) or a salt thereof is acetylated, palmitoylated, propanoylated, pivaloylated, succinylated, fumarylated, alanylated or dimethylaminomethylcarbonylated); and that the carboxyl group of the compound of the present invention or a salt thereof is, for example, esterified or amidated (e.g., compounds in which the carboxyl group of the compound represented by formula (I) or a salt thereof is made into ethyl ester, phenyl ester, phenylethyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide). Those compounds may be produced by a known method per se. The prodrug of the compound represented by formula (I) or a salt thereof may be either a hydrate or a non-hydrate.

With regard to $R^1$ in formula (I), C1-4 alkoxy which is a prodrug is preferred besides the hydroxy group. More preferably, it is hydroxy, methoxy, ethoxy or the like, and, most preferably, it is hydroxy.

With regard to $R^2$ and $R^3$, any of the groups is preferred and preferred examples include chlorine, hydrogen, C3-7 alkyl or C3-7 alkyl in which one carbon atom is substituted with one to three fluorine atom(s), more preferred examples include chlorine, hydrogen, propyl, hexyl, 3,3,3-trifluoropropyl, 4,4,4-trifluorobutyl and 5,5,5-trifluoropentyl, and most preferred ones are hydrogen, propyl and hexyl.

In the compound of the present invention, examples of preferred ones include (1) 2-propyloctanoic acid, (2) 2-hexylpent-4-enoic acid, (3) 2-hexylpent-4-ynoic acid, (4) 2-propylpentanoic acid, (5) 2-ethylhexanoic acid, (6) 2-propylheptanoic acid, (7) 2-propylhexanoic acid, (8) 2-propyldecanoic acid, (9) 2-propylpent-4-enoic acid, (10) 5-methyl-2-propylhexanoic acid, (11) 4-methyl-2-propylpentanoic acid, (12) 5,5-dimethyl-2-propylhexanoic acid, (13) 6,6-dimethyl-2-propylheptanoic acid, (14) 5-ethyl-2-propylheptanoic acid, (15) 7-methyl-2-propyloctanoic acid, (16) 6-methyl-2-propylheptanoic acid, (17) 2-propyloct-7-enoic acid, (18) (2E)-2-propylpent-2-enoic acid, (19) 5-fluoro-2-propylpentanoic acid, (20) 5,5-difluoro-2-propylpentanoic acid, (21) 5,5,5-trifluoro-2-propylpentanoic acid, (22) 7,7-difluoro-2-propylheptanoic acid, (23) 8,8-difluoro-2-propyloctanoic acid, (24) 6,6,6-trifluoro-2-propylhexanoic acid, (25) 7-fluoro-2-propylheptanoic acid, (26) 8-fluoro-2-propyloctanoic acid, (27) 6-fluoro-2-propylhexanoic acid, (28) 6,6-difluoro-2-propylhexanoic acid, (29) 9-fluoro-2-propylnonanoic acid, (30) 9,9-difluoro-2-propylnonanoic acid, (31) 8,8,8-trifluoro-2-propyloctanoic acid, (32) 7,7,7-trifluoro-2-propylheptanoic acid, (33) 7-chloro-2-propylheptanoic acid, (34) 2-chloro-2-propylpentanoic acid, (35) 2-ethoxypentanoic acid, (36) 2-propoxypentanoic acid, (37) 2-butoxypentanoic acid, (38) 2-(2-ethoxyethyl)pentanoic acid, (39) 2-(2-methoxyethyl) pentanoic acid, (40) 5-methoxy-2-propylpentanoic acid, (41) 2-(pentyloxy)pentanoic acid, (42) 5-ethoxy-2-propylpentanoic acid, (43) 2-(hexyloxy)pentanoic acid, (44) 6-methoxy-2-propylhexanoic acid, (45) 2-(pentylthio)pentanoic acid, (46) 5-cyclohexyl-2-propylpentanoic acid, (47) 5-phenyl-2-propylpentanoic acid, (48) 5-phenoxy-2-pro pylpentanoic acid, (49) 6-phenyl-2-propylhexanoic acid, (50) 2-(2-cyclohexylethyl)pentanoic acid, (51) 2-(cyclohexylmethyl) pentanoic acid, (52) 2-benzylpentanoic acid, (53) 2-cyclohexylpentanoic acid, (54) 2-cyclopentylpentanoic acid, (55) 2-phenylpentanoic acid, (56) 2-phenoxypentanoic acid, (57) 1-(2-propyloctanoyl)piperidine, (58) 4-(2-propyloctanoyl)morpholine, (59) 2-propyloctanamide, (60) N-isoproyl-2-propyloctanamide, (61) N,N-dimethyl-2-propyloctanamide, (62) 6,6,6-trifluoro-N-(4-methoxyphenyl)-2-propylhexanamide, (63) N-benzyl-6,6,6-trifluoro-2-propylhexanamide, (64) 6,6,6-trifluoro-2-propyl-N-pyridin-3-ylhexanamide, (65) (2S)-2-[(6,6,6-trifluoro-2-propylhexanoyl)amino]propanoic acid, (66) N-methyl-2-propylpentanamide, (67) N,N-dimethyl-2-propylpentanamide, (68) 2-propyl-4-hexynoic acid, (69) 7-oxo-2-propyloctanoic acid, (70) 7-hydroxy-2-propyloctanoic acid, (71) 8-hydroxy-2-propyloctanoic acid, (72) 2-propylsuberic acid, (73) 6-hydroxy-2-propyloctanoic acid, (74) 6-oxo-2-propyloctanoic acid, (75) 2-(2-hydroxypropyl)octanoic acid, (76) 2-(2-oxoproyl)octanoic acid, (77) 2-(3-hydroxypropyl)octanoic acid and optical isomers thereof.

More preferred examples include (1) 2-propyloctanoic acid, (2) 2-hexylpent-4-enoic acid, (3) 2-hexylpent-4-ynoic acid, (4) 2-propylpentanoic acid, (5) 2-ethylhexanoic acid, (6) 2-propylheptanoic acid, (7) 2-propylhexanoic acid, (8) 2-propyldecanoic acid, (68) 2-propyl-4-hexynoic acid, (69) 7-oxo-2-propyloctanoic acid, (70) 7-hydroxy-2-propyloctanoic acid, (71) 8-hydroxy-2-propyloctanoic acid and optically active substances thereof, salt thereof and prodrug thereof.

Particularly preferred examples include (1) 2-propyloctanoic acid, (1-1) (2R)-2-propyloctanoic acid, (1-2) (2S)-2-propyloctanoic acid, (2) 2-hexylpent-4-enoic acid, (2-1) (2R)-2-hexylpent-4-enoic acid, (2-2) (2S)-2-hexylpent-4-enoic acid, (3) 2-hexylpent-4-ynoic acid, (3-1) (2R)-2-hexylpent-4-ynoic acid, (3-2) (2S)-2-hexylpent-4-ynoic acid, (4) 2-propylpentanoic acid, (5) 2-ethylhexanoic acid, (5-1) (2R)-2-ethylhexanoic acid, (5-2) (2S)-2-ethylhexanoic acid, (68) 2-propyl-4-hexynoic acid, (68-1) (2R)-2-propyl-4-hexynoic acid, (68-2) (2S)-2-propyl-4-hexynoic acid, (69) 7-oxo-2-propyloctanoic acid, (69-1) (2R)-7-oxo-2-propyloctanoic acid, (69-2) (2S)-7-oxo-2-propyloctanoic acid, (70) 7-hydroxy-2-propyloctanoic acid, (70-1) (2R,7R)-7-hydroxy-2-propyloctanoic acid, (70-2) (2R,7S)-7-hydroxy-2-propyloctanoic acid, (70-3) (2S,7R)-7-hydroxy-2-propyloctanoic acid, (70-4) (2S,7S)-7-hydroxy-2-propyloctanoic acid, (71) 8-hydroxy-2-propyloctanoic acid, (71-1) (2R)-8-hydroxy-2-propyloctanoic acid, (71-2) (2S)-8-hydroxy-2-propyloctanoic acid, salt thereof and prodrug thereof.

Process for Preparation of the Compound of the Present Invention:

The compound of the present invention has been known per se or can be prepared by a known process (in the case of the compound represented by formula (I), for example, by the process mentioned in EP-A-0632008, WO 99/58513, WO 00/48982, WO 03/051852, WO 03/097851, etc.) such as a process mentioned in *Comprehensive Organic Transformations: A Guide to Functional Group Preparations,* 2nd Edition (Richard C. Larock, John Wiley & Sons Inc., 1999) or by an appropriate combination of the process as such.

Toxicity:

Toxicity of the compound of the present invention is sufficiently low and has been confirmed to be sufficiently safe for using as a medicament. For example, in a single intravascular administration using dogs, no dead case was noted in (2R)-2-propyloctanoic acid at 100 mg/kg.

Application to Medicaments:

In animals including humans and particularly in humans, the compound of the present invention suppresses nerve cell death as a substance for acceleration of grafting, differentiation, growth and/or maturation of stem cells, nerve precursor cells or nerve cells or as a potentiator for neurotrophic factor activity, neurotrophic factor-like substance or neurodegenerative suppressor and accelerates repair and regeneration of nerve tissues by neogenesis, regeneration and/or axon evolution. In addition, the compound of the present invention is useful for preparation from brain tissues, bone marrow and/or embryonic stem cells of cells for transplant (e.g., nerve stem cells, nerve precursor cells, nerve cells, etc.) and also accelerates grafting, growth, differentiation and/or maturation of cells for transplant (e.g., nerve stem cells, nerve precursor cells, nerve cells, etc.) whereupon it is useful for prevention, treatment and/or suppression of progression, of neurodegenerative diseases. To be more specific, it is useful for prevention, treatment and/or suppression of progression, of, for example, Parkinson's disease or Parkinson syndrome, Alzheimer's disease, Down's disease, amyotrophic lateral sclerosis, familial amyotrophic lateral sclerosis, progressive supranuclear palsy, Huntington's disease, spinocerebellar ataxia, dentatorubral-pallidoluysian atrophy, olivopontocerebellar atrophy, cortical basal nucleus denaturation, familial dementia, frontotemporal dementia, senile dementia, diffuse Lewy body disease, striatonigral degeneration, chorea athetosis, dystonia, Meige syndrome, late cortical cerebellar atrophy, familial spastic paraplegia, kinesioneurosis, McArdle-Joseph's disease, Pick's disease, stroke or cerebrovascular accident (e.g., cerebral infarction after cerebral hemorrhage or subarachnoid hemorrhage or after cerebral thrombus or embolization, nerve function disorder after cerebral infarction, etc.), nerve function disorder after wound of cerebral bone marrow, nerve function disorder by toxin (e.g., arsenic, cadmium, organic mercury, etc.), toxic gas (e.g., sarin, soman, tabun, VX gas, etc.), radioactivity or the like, demyelinating disease (e.g., multiple sclerosis, Guillain-Barre syndrome, acute disseminated cerebrospinal meningitis, acute cerebellitis, transverse myelopathy, etc.), cerebral tumor (e.g., astrocytic sarcoma, etc.), cerebrospinal diseases accompanied by infectious diseases (e.g., meningitis, cerebral abscess, Creutzfeldt-Jakob disease, AIDS (HIV) dementia, etc.), psychotic diseases (e.g., schizophrenia, manic-depressive illness, neurosis, psychosomatic disorder, etc.), sleep disorder (e.g., narcolepsy, primary hypersomnia, recurrent hypersomnia, idiopathic hypersomnia, insomnia, etc.), epilepsy, and the like.

In addition, as mentioned above, the compound of the present invention is also useful for the preparation from the living body such as brain tissues, bone marrow and/or embryonic stem cells and can be used as an additive for in vitro culturing or, preferably, as a accelerator for growth and differentiation of nerve stem cells for transplant, nerve precursor cells for transplant, nerve cells for transplant, mature nerve cells for transplant, or the like. Here, the transplant is not limited to autologous transplant but heterologous transplant may be acceptable as well. With regard to cells for transplant, nerve stem cells and nerve precursor cells are preferred.

Furthermore, the compound of the present invention acts on cells where differentiation stage is more progressed than nerve stem cells or particularly on glia cells (such as astrocytes, oligodendrocytes, microglia and ependymal cells) or glial precursor cells and can be differentiated into nerve cells and further into mature nerve cells. With regard to mechanism of differentiation from those cells to nerve cells and mature nerve cells, any mechanism will do and its example is a mechanism in which glia cells or glial precursor cells as such become nerve stem cells or nerve precursor cells being mediated, for example, by immaturation and then differentiated and grown to nerve cells or mature nerve cells.

In using the compound of the present invention for the above-mentioned object, in humans and animals, it is usually administered either systemically or locally and either orally or parenterally while, in cultured cells, it is treated by adding to a culturing liquid or directly injecting into the cells. When it is administered to the living body, surgical means such as a direct administration to cerebral ventricle is also possible.

Although the dose may vary depending upon age, body weight, symptom, therapeutic effect, administration method, treating time, etc., it is usual in the case of oral administration that a dose within a range of 1 μg to 5,000 mg is orally administered for one to several times a day to an adult. In the case of parenteral administration, a dose within a range of 0.1 ng to 500 mg is parenterally administered for one to several times a day to an adult. Dosage form for parenteral administration is preferably an intravenous administration and it is continuously administered into vein within a range of 1 hour to 24 hours a day.

In the case of cultured cells, it is added to a culturing liquid within a range of 1 μmol/L to 100 mmol/L or directly injected into the cells within a range of 0.1 fmol/L to 100 μmol/L (such as microinjection).

Of course, as mentioned before, dose for administration and treatment varies depending upon various conditions and, therefore, there are some cases where less dose than the above-mentioned administering/treating dose is sufficient or there are some other cases where more dose than the above range is to be administered/treated.

In administration of the compound of the present invention, it is used as a solid preparation for internal application and a liquid preparation for internal application for an object of oral administration and also as an injection, an agent for external application, a suppository, an eye drop, an inhalation agent, a nasal agent, etc. for an object of parenteral administration.

The solid preparation for internal application for an object of oral administration includes tablets, pills, capsules, diluted powders, granules and the like. The capsules include hard capsules and soft capsules. The tablets include sublingual tablets, tablets sticking in the mouth, quickly disintegrating tablets in the mouth and the like.

In the solid preparation for internal application as such, one or more active substances are used by making into pharmaceutical preparation by a conventional method either as they are or by mixing with excipients (e.g., lactose, mannitol, glucose, microcrystalline cellulose, starch, etc.), binders (e.g., hydroxypropyl cellulose, polyvinylpyrrolidone, magnesium metasilicate aluminate, etc.), disintegrating agents (e.g., calcium cellulose glycolate, etc.), lubricants (e.g., magnesium stearate, etc.), stabilizers, dissolving aids (e.g., glutamic acid and aspartic acid, etc.) and the like. If necessary, the solid preparation may be coated with a coating agent (e.g., sugar, gelatin, hydroxypropyl cellulose, hydroxypropyl methylcellulose phthalate, etc.) or may be coated with two or more layers. Capsules of a substance which can be absorbed such as gelatin are also included therein.

The sublingual tablets are prepared according to a known method. For example, one or more active substances are mixed with excipients (e.g., lactose, mannitol, glucose, microcrystalline cellulose, colloidal silica, starch, etc.), binders (e.g., hydroxypropyl cellulose, polyvinylpyrrolidone, magnesium metasilicate aluminate, etc.), disintegrating agent (e.g., starch, L-hydroxypropyl cellulose, carboxymethyl cellulose, croscarmellose sodium, calcium cellulose glycolate, etc.), lubricant (e.g., magnesium stearate, etc.), swelling agent (e.g., hydroxypropyl cellulose, hydroxypropyl methylcellulose, Carbopol, carboxymethyl cellulose, polyvinyl alcohol, xanthan gum, guar gum, etc.), swelling aids (e.g., glucose, fructose, mannitol, xylitol, erythritol, maltose, trehalose, phosphate, citrate, silicate, glycine, glutamic acid, arginine, etc.), stabilizers, dissolving aids (e.g., polyethylene glycol, propylene glycol, glutamic acid, aspartic acid, etc.), fragrances (e.g., orange, strawberry, mint, lemon, vanilla, etc.) and the like, and used by making into a pharmaceutical preparation by a conventional method. If necessary, the tablets may be coated with a coating agent (e.g., sugar, gelatin, hydroxypropyl cellulose, hydroxypropyl methylcellulose phthalate, etc.) or may be coated with two or more layers If necessary, it is possible to add commonly used additives such as antiseptics, antioxidants, coloring agents and sweeteners.

The tablets sticking in the mouth is prepared according to a known method. For example, one or more active substances are mixed with excipients (e.g., lactose, mannitol, glucose, microcrystalline cellulose, colloidal silica, starch, etc.), binders (e.g., hydroxypropyl cellulose, polyvinylpyrrolidone, magnesium metasilicate aluminate, etc.), disintegrating agents (e.g., starch, L-hydroxypropyl cellulose, carboxymethyl cellulose, croscarmellose sodium, calcium cellulose glycolate, etc.), lubricants (e.g., magnesium stearate, etc.), sticking agents (e.g., hydroxypropyl cellulose, hydroxypropyl methylcellulose, Carbopol, carboxymethyl cellulose, polyvinyl alcohol, xanthan gum, guar gum, etc.), sticking aids (e.g., glucose, fructose, mannitol, xylitol, erythritol, maltose, trehalose, phosphate, citrate, silicate, glycine, glutamic acid, arginine, etc.), stabilizers, dissolving aids (e.g., polyethylene glycol, propylene glycol, glutamic acid, aspartic acid, etc.), fragrances (e.g., orange, strawberry, mint, lemon, vanilla, etc.), and the like, and used by making into a pharmaceutical preparation by a conventional method. If necessary, the tablets may be coated with a coating agent (such as sugar, gelatin, hydroxypropyl cellulose and hydroxypropyl methylcellulose phthalate) or may be coated with two or more layers. If necessary, it is possible to add commonly used additives such as antiseptics, antioxidants, coloring agents and sweeteners.

The quickly disintegrating tablets in the mouth is prepared according to a known method. For example, one or more active substances as they are or are mixed with appropriate coating agents (e.g., ethylcellulose, hydroxypropyl cellulose, hydroxypropyl methylcellulose, acrylate/methacrylate copolymer, etc.) and plasticizers (e.g., polyethylene glycol, triethyl citrate, etc.). The resulting coated active substance powders or granulated powder particles are mixed with excipients (e.g., lactose, mannitol, glucose, microcrystalline cellulose, colloidal silica, starch, etc.), binders (e.g., hydroxypropyl cellulose, polyvinylpyrrolidone, magnesium metasilicate aluminate, etc.), disintegrating agent (e.g., starch, L-hydroxypropyl cellulose, carboxymethyl cellulose, croscarmellose sodium, calcium cellulose glycolate, etc.), lubricant (e.g., magnesium stearate, etc.), dispersing aid (e.g., glucose, fructose, mannitol, xylitol, erythritol, maltose, trehalose, phosphate, citrate, silicate, glycine, glutamic acid, arginine, etc.), stabilizers, dissolving aids (e.g., polyethylene glycol, propylene glycol, glutamic acid, aspartic acid, etc.), fragrances (e.g., orange, strawberry, mint, lemon, vanilla, etc.), and the like, and used by making into a pharmaceutical preparation by a conventional method. If necessary, the tablets may be coated with a coating agent (e.g., sugar, gelatin, hydroxypropyl cellulose, hydroxypropyl methylcellulose phthalate, etc.) or may be coated with two or more layers. If necessary, it is possible to add commonly used additives such as antiseptics, antioxidants, coloring agents and sweeteners.

The liquid preparation for internal application with an object of oral administration includes a pharmaceutically acceptable aqueous preparation, a suspension, an emulsion, a syrup, an elixir and the like. In such a liquid preparation, one or more active substances are dissolved, suspended or emulsified in a commonly used diluent (e.g., pure water, ethanol, a mixed solution thereof, etc.). The liquid preparation may further contain moisturizers, suspending agents, emulsifiers, sweeteners, flavors, aromatizing agents, preservatives, buffers and the like.

Dosage form of agent for external application with an object of parenteral administration includes, for example, ointments, gels, creams, poultices, sticking agents, liniments, sprinkling agents, inhaling agents, sprays, aerosols, eye drops and nasal agents. Each of them contains one or more active substances and is manufactured by a known method or a conventionally used formulation.

The ointments are manufactured by a known or commonly used formulation. For example, one or more active substances are mixed or melted with a substrate. A substrate for the ointments is selected from known or commonly used ones. For example, one which is selected from the following is used solely or two or more thereof are used by mixing. For example, they are higher fatty acid or higher fatty acid esters (e.g., adipic acid, myristic acid, palmitic acid, stearic acid, oleic acid, adipate, myristate, palmitate, stearate, oleate, etc.), waxes (e.g., beeswax, whale wax, ceresin, etc.), surfactants (e.g., polyoxyethylene alkyl ether phosphate, etc.), higher alcohols (e.g., cetanol, stearyl alcohol, cetostearyl alcohol, etc.), silicone oils (e.g., dimethyl polysiloxane, etc.), hydrocarbon (e.g., hydrophilic vaseline, white vaseline, pure lanolin, liquid paraffin, etc.), glycols (e.g., ethylene glycol, diethylene glycol, propylene glycol, polyethylene glycol, Macrogol, etc.), plant oils (e.g., castor oil, olive oil, sesame oil, turpentine oil, etc.), animal oils (e.g., mink oil, egg yolk oil, squalane, squalene, etc.), water, absorption promoters and skin rash preventing agents. Moisturizers, preservatives, stabilizers, antioxidants, fragrances and the like may be further contained therein.

The gel preparations can be manufactured by a known or a conventionally used formulation. For example, they are prepared by melting one or more active substances with a substrate. The gel substrate is selected from known or commonly used ones. For example, one which is selected from the following is used solely or two or more thereof are used by mixing. For example, they are lower alcohols (e.g., ethanol, isopropanol, etc.), gelling agents (e.g., carboxymethyl cellulose, hydroxyethyl cellulose, hydroxypropyl cellulose, ethylcellulose, etc.), neutralizing agents (e.g., triethanolamine, diisopropanolamine, etc.), surfactants (e.g., polyethylene glycol monostearate, etc.), gums, water, absorption promoters and preventing agents for skin rash. Preservatives, antioxidants, fragrances and the like may also be contained therein.

The cream preparations can be manufactured by a known or a conventionally used formulation. For example, they are prepared by melting or emulsifying one or more active substances in a substrate. The cream substrate is selected from known or commonly used ones. For example, one which is selected from the following is used solely or two or more thereof are used by mixing. For example, they are higher fatty acid esters, lower alcohols, hydrocarbons, polyhydric alcohols (e.g., propylene glycol, 1,3-butylene glycol, etc.), higher alcohols (e.g., 2-hexyldecanol, cetanol, etc.), emulsifiers (e.g., polyoxyethylene alkyl ether, fatty acid ester, etc.), water, absorption promoters and preventive agents for skin rash. Preservatives, antioxidants, fragrance and the like may also be contained therein.

The poultice preparations can be manufactured by a known or a conventionally used formulation. For example, they are manufactured by melting one or more active substances with a substrate as a kneaded product and extending and applying it on a support. The poultice substrate is selected from known or commonly used ones. For example, one which is selected from the following is used solely or two or more thereof are used by mixing. For example, they are thickeners (e.g., polyacrylic acid, polyvinylpyrrolidone, gum arabic, starch, gelatin, methylcellulose, etc.), moisturizer (e.g., urea, glycerol, propylene glycol, etc.), bulking agents (e.g., kaolin, zinc oxide, talc, calcium, magnesium, etc.), water, dissolving aids, sticking agents and preventive agents for skin rash. Preservatives, antioxidants, fragrances and the like may also be contained therein.

The sticking preparations can be manufactured by a known or a conventionally used formulation. For example, they are prepared by melting one or more active substances with a substrate and extending and applying it on a support. The substrate for sticking preparation is selected from known or commonly used ones. For example, one which is selected from the following is used solely or two or more thereof are used by mixing. For example, they are a polymer substrate, fats and oils, higher fatty acids, sticking agents and preventive agents for skin rash. Preservatives, antioxidants, fragrances and the like may also be contained therein.

The liniment preparations can be manufactured by a known or a conventionally used formulation. For example, they are prepared by dissolving, suspending or emulsifying one or more active substances in one or more which are selected from water, alcohols (e.g., ethanol, polyethylene glycol, etc.), higher fatty acids, glycerols, soaps, emulsifiers, suspending agents and the like. Preservatives, antioxidants, fragrance and the like may also be contained therein.

The sprinkling preparations, inhaling preparations and spray preparations may contain, in addition to commonly used diluents, buffers which give isotonicity to stabilizer such as sodium hydrogen sulfite (e.g., isotonizing agents such as sodium chloride, sodium citrate or citric acid). Methods for the manufacture of spray preparations are mentioned in detail in, for example, U.S. Pat. Nos. 2,868,691 and 3,095,355.

The injection preparations for parenteral administration include all injection preparations. For example, they include injection preparations into muscle, injection preparation into vein and infusion preparations into vein.

The injection preparations for parenteral administration includes injection preparations in a solution, a suspension or an emulsion and a solid which is used by dissolving or suspending it in a solvent upon use. The injection preparations are used in such a manner that one or more active substances are dissolved, suspended or emulsified in a solvent. The solvent includes, for example, distilled water for injection, a physiological saline, plant oils, alcohols such as propylene glycol, polyethylene glycol and ethanol and a combination thereof. The injection preparation may also contain stabilizers, dissolving aids (e.g., glutamic acid, aspartic acid, Polysolvate 80 (registered trade mark)), suspending agents, emulsifiers, analgesic agents, buffers, preservatives and the like. Those are prepared either by sterilization or by aseptic operation in the final step. It is also possible that aseptic solid preparations such as freeze-dried products are manufactured and, before use, they are dissolved in aseptic distilled water for injection or in other solvent.

The inhaling preparations for parenteral administration include aerosol preparations, powder preparations for inhalation or liquid preparations for inhalation and the liquid preparations for inhalation may be in such a form that, upon use, they are dissolved or suspended in water or in other appropriate solvent.

The inhaling preparations as such are manufactured according to a known method. In the case of the liquid preparations for inhalation, for example, antiseptics (e.g., benzalkonium chloride, paraben), coloring agents, buffers (e.g., sodium phosphate, sodium acetate, etc.), isotonizing agents (e.g., sodium chloride, concentrated glycerol, etc.), thickeners (e.g., carboxyvinyl polymer, etc.), absorption promoters and the like may be appropriately selected upon necessity to prepare. In the case of powder preparations for inhalation, lubricants (e.g., stearic acid, salts thereof, etc.), a binding agents (e.g., starch, dextrin, etc.), excipients (e.g., lactose, cellulose, etc.), coloring agents, antiseptics (e.g., benzalkonium chloride, paraben, etc.), absorption promoters and the like are appropriately selected upon necessity to prepare. In administration of the liquid preparations for inhalation, a sprayer (e.g., atomizer, nebulizer, etc.) is usually used while, in administration of powder preparations for inhalation, administering device for powdery medicament is usually used.

Other compositions for parenteral administration include suppository for intrarectal administration, pessary for intravaginal administration and the like, containing one or more active substances and being formulated by a conventional method.

The compound of the present invention may be administered as a combined preparation in combination with other medicament for the object of (1) supplement and/or potentiation of preventive and/or treating effects, (2) improvement in kinetics and absorption or reduction of dosage, and/or (3) reduction in side effects of the compound.

It is also possible that the compound of the present invention is combined and administered as a combined preparation for the object of (1) supplement and/or potentiation of preventive and/or treating effects, (2) improvement in kinetics and absorption or reduction of dosage, and/or (3) reduction in side effects of other medicament used together.

The combined preparation of the compound of the present invention with other medicament (hereinafter, referred to as the combined preparation of the present invention) may be administered in a form in which both components are compounded in a preparation or in a form where different preparations are prepared and administered. When different preparations are prepared and administered as such, they may be administered by administration at the same time and administration with interval of time.

In the case of administration with interval of time, the compound of the present invention may be firstly administered and then other medicament may be administered, alternatively, other medicament may be firstly administered and then the compound of the present invention may be administered. Methods of administration for each of them are the same or different.

There is no particular limitation for the disease for which the combined preparation of the present invention achieves preventive and/or treating effects and the diseases may be such a one that a preventive and/or treating effect is supplemented and/or potentiated as compared with the case where each is administered solely.

Examples of other medicament used for the combined preparation of the present invention include an acetylcholine esterase inhibitor, a nicotinic receptor regulator, a suppressor for production, secretion, accumulation, aggregation and/or sedimentation of β amyloid protein (such as a β secretase inhibitor, a γ secretase inhibitor, a β amyloid protein aggregation inhibitor, a β amyloid vaccine and a β amyloid protease), a brain function activator, other treating drugs for Parkinson's disease (such as a dopamine receptor agonist, a monoamine oxidase (MAO) inhibitor, an anticholinergic drug and a catechol-O-methyltransferase (COMT) inhibitor), a drug for treating amyotrophic lateral sclerosis, a drug for treating hyperlipidemia such as a cholesterol lowering agent (e.g., statin type, fibrate type and squalene synthase inhibitor), a drug for treating abnormal behavior, poriomania or the like accompanied with progress of dementia, an apoptosis inhibitor, a drug for accelerating nerve differentiation and/or regeneration, an antihypertensive drug, a drug for treating diabetes, an antidepressant drug, an antianxiety drug, a nonsteroidal anti-inflammatory drug, a disease modifying anti-rheumatic drug, an anticytokine drug (e.g., TNF inhibitor, MAP kinase inhibitor, etc.), a steroid drug, a sex hormone or derivatives thereof, parathyroid hormone (e.g., PTH, etc.) and a calcium acceptor antagonist.

Examples of the acetylcholine esterase inhibitor include donepezil, rivastigmine, galanthamine, zanapezil (TAK 147) and the like.

Examples of the β secretase inhibitor include 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl)-methoxytetralin, 6-(4-biphenylyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, optically active substances thereof, salts thereof, hydrates thereof, OM 99-2 (WO 01/00663) and the like.

Examples of the β amyloid protein aggregation inhibitor include PTI-00703, ALZHEMED (NC-531), PPI-368 (JP-A-11-514333), PPI-558 (JP-A-2001-500852), SKF-74652 (*Biochem. J.*, 340(1), 283-289 (1990)) and the like.

Examples of the brain function activator include aniracetam, nicergoline and the like.

Examples of the dopamine receptor agonist include L-dopa, bromocriptine, pergolide, talipexole, pramipexole, cabergoline, amantadine and the like.

Examples of the monoamine oxidase (MAO) inhibitor include safrazine, deprenyl, selegiline, remacemide, riluzole and the like.

Examples of the anticholinergic drug include trihexylphenidyl, biperiden and the like.

Examples of the catechol-O-methyltransferase inhibitor include entacapone and the like.

Examples of the drug for treating amyotrophic lateral sclerosis include riluzole, neurotrophic factor and the like.

Examples of the statin type drug for treating hyperlipidemia include pravastatin sodium, atorvastatin, simvastatin, losbastatin and the like.

Examples of the fibrate type drug for treating hyperlipidemia include clofibrate and the like.

Examples of the apoptosis inhibitor include CPI-1189, IDN-6556, CEP-1347 and the like.

Examples of the drug for accelerating nerve differentiation and/or regeneration include leteprinim, xaliproden (SR-57746-A), SB-216763 and the like.

Examples of the nonsteroidal anti-inflammatory drug include meloxicam, tenoxicam, indomethacin, ibuprofen, celecoxib, rofecoxib, aspirin, indomethacin and the like.

Examples of the steroid drug include dexamethasone, hexestrol, cortisone acetate and the like.

Examples of the sex hormone or derivatives thereof include progesterone, estradiol, estradiol benzoate and the like.

The above medicaments are merely exemplified and the combined preparation of the present invention is not limited thereto.

Dose and administering method of the compound of the present invention in the combined preparation of the present invention are the same as those mentioned already.

There is no particular limitation for the ratio by weight of the compound of the present invention to other medicament. With regard to other medicament, any two or more thereof may be used in combination. Moreover, other medicament which supplements and/or potentiates the preventive and/or treating effects of the compound of the present invention includes not only that which has been found up to now but also that which will be found in future on the basis of the above-mentioned mechanism.

EFFECTS OF THE INVENTION

Since the compound of the present invention has a accelerating action for nerve regeneration for animals including humans and particularly in humans, it is useful for prevention and/or treatment of neurodegenerative diseases, and it can be utilized as medicaments. In addition, since the compound of the present invention is used as an additive for culturing in preparation of nerve cells for transplant in vitro to thereby efficiently prepare nerve cells, it can be utilized for preparation of cells having pharmaceutical use. For example, the compound of the present invention may be administered to the living body so that endogenous cells are differentiated, grown or matured with an object of prevention and/or treatment of neurodegenerative diseases and, after nerve stem cells, nerve precursor cells or nerve cells are transplanted into the living body, the compound of the present invention may be administered to the living body whereby those cells are grafted, differentiated, grown and/or matured. It is also possible that the transplant cells are cultured and appropriately differentiated and grown in the presence of the compound of the present invention in vitro and then they are transplanted into the living body. In addition, since nerve cells and mature nerve cells can be prepared even from non-nerve cells such as glia cells in accordance with the present inventions those cells can be prepared in large quantities. Furthermore, in the present invention, large quantities of nerve cells and mature nerve cells can be prepared from one's own cells or from cell materials in a small amount collected from one's own body and, therefore, there is no ethical problem.

BEST MODE FOR CARRYING OUT THE INVENTION

The present invention will now be illustrated in detail by way of the following Examples; however, the present invention is not limited thereto.

The fact that the compound of the present invention has a regeneration effect for nerve and an improving effect for pathology was proved by the following experiments. With regard to a measuring method for evaluating the compound of the present invention, the following improvement was done for an object of improving the measuring precision and/or measuring sensitivity. Detailed experimental methods will be shown as hereunder.

Example 1

Investigation of the Effect on In Vivo Nerve Stem Cell Differentiation
1-A: Evaluation by Histological Observation
1-A-1: Preparation of a Four-Vein Ligated (4VO) Rat Model A four-vein ligated (4VO) rat model was prepared by a partially modified method by Prusinery, et al. (*J. Cereb. Blood Flow Metab.*, 16, 973-980 (1979)). Thus, vertebral arteries on both sides of male rat of Wistar strain were permanently obstructed and, on the next day, whole carotid artery was exposed and was temporally obstructed for 10 minutes using a clip. Rats where no response was noted immediately after obstruction of whole carotid arteries on both sides and forward-facing response disappeared were used for the experiment.
1-A-2: Evaluation of Nerve Regeneration Action
1-A-2-1: Evaluation by Nissl Staining Evaluation of nerve cell regeneration was conducted by preparing brain tissue sample by Nissl staining and counting nerve cell numbers in right and left hippocampus CA1 regions. Administration of medium (0.1 vol % of Tween 80) and a test compound (10 mg/kg) was conducted by a compulsory oral administration once daily for 40 days from the 8th day after the 4VO treatment where petrosal nerve cells of hippocampus CA1 region showed a retarded nerve cell death.
Result:

The result was that, as compared with normal group, petrosal nerve cell numbers existing in hippocampus CA1 region significantly decreased in a group treated with a medium subjected to forebrain ischemia for 10 minutes.

Figure 1:
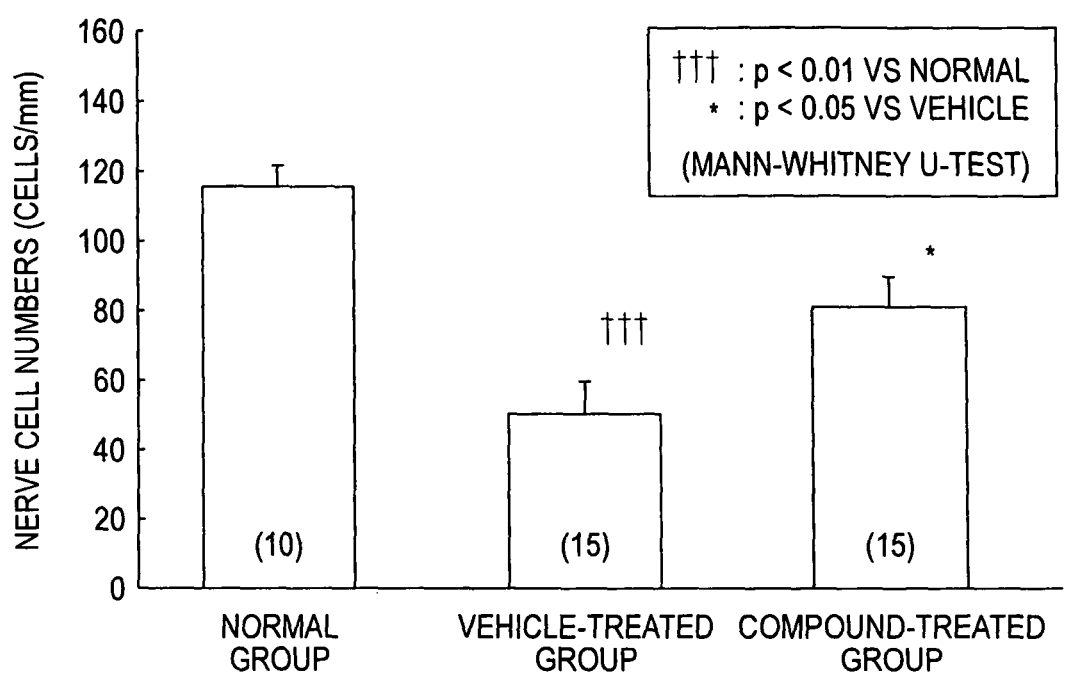
FIG. 1 shows changes in living petrosal nerve cell numbers in a four-vein ligated (4VO) rat model to which (2R)-2-propyloctanoic acid was administered.

For example, the result when (2R)-2-propyloctanoic acid was used as a test compound is shown in FIG. 1.
1-A-2-2: Evaluation of BrdU and NeuN by a Double Immunostaining Confirmation of the fact that petrosal nerve cells increased in Example 1-A-2-1 were regenerated nerve cells was conducted by preparing a brain tissue sample immunostained with BrdU and NeuN and counting nerve cell numbers which were positive to double staining in right and left hippocampus CA1 region. Incidentally, anti-NeuN antibody was used for the purpose of detection of mature nerve cells while BrdU and anti-BrdU antibody were used for the purpose of detection of newly born cells. Administration of the medium (0.5 vol % of Tween 80) and the test compound (10 mg/kg) was conducted in the same manner as above. Administration of BrdU was conducted by intraperitoneal administration (50 mg/kg) once daily during the period of immediately after blood reperfusion in the 4VO treatment until excision of the tissue. Nerve cell numbers which were positive to double staining were calculated as number per unit length (mm) using nerve cell layer length of the hippocampus CA1 region and nerve cell numbers which were positive to double staining.
Result:

The result was that, as compared with a group to which a medium was administered, there was a significant increase in cells existing in hippocampus CA1 region which were positive to double staining by anti-BrdU antibody and anti-NeuN antibody in a group to which the compound was administered.

For example, there were 2.5±0.7 cells which were positive to double staining per mm in a group (n=13) treated with a medium while, in a group (n=13) to which the test compound was added, there were 5.7±1.2 cells/mm (p=0.0322; t-test) when (2R)-2-propyloctanoic acid was used as a test compound.

1-B: Evaluation by a Behavior Pharmacological Test

1-B-1: Preparation of Four-Vein Ligated (4VO) Rat Model and Administration of the Medicament A four-vein ligated (4VO) rat model was prepared according to a method mentioned in Example 1-A-1 and subjected to the following test. Incidentally, administration of a medium (0.1 vol % of Tween 80) and a test compound ((2R)-2-propyloctanoic acid; 1, 3, 10 mg/kg) was conducted by a compulsorily repeated oral administration of five days a week from 8 days after the 4VO treatment where petrosal nerve cells of hippocampus CA1 region surely showed a retarded nerve cell death until 48 days thereafter. Group constitutions are shown in the following Table 1.

TABLE 1

| Groups | 4VO treatment | Treatment with agent | Case numbers |
|---|---|---|---|
| Normal group | not treated | Medium | 18 |
| Control group | treated | Medium | 20 |
| 1 mg/kg group | treated | (2R)-2-propyloctanoic acid, 1 mg/kg, oral administration | 22 |
| 3 mg/kg group | treated | (2R)-2-propyloctanoic acid, 3 mg/kg, oral administration | 22 |
| 10 mg/kg group | treated | (2R)-2-propyloctanoic acid, 10 mg/kg, oral administration | 20 |

1-B-2: Evaluation in Water Maze Learning Test

In the water maze learning test, a black circular pool (manufactured by Neuroscience) of 150 cm diameter and 50 cm height was used. The pool was filled with tap water of about 23° C. to a height of about 30 cm (platform surface was about 1 cm beneath the water surface). The platform (made of colorless and transparent acrylate; circular shape having 10 cm diameter) which was to be a goal was placed in a distance of about 35 cm from the inner wall of the pool. During the test period, positions of things which were hints for recognition of space such as racks, illumination instruments and persons who conducted the experiments were made constant and illumination level was made constant as well.

Rats on the third day after completion of repetitive administrations were allowed to stand at a starting position and the time until they climbed up to the platform (escape latency (seconds)) was measured. Maximum swimming time for climbing up to the platform was made 90 seconds and, when a rat climbed up to the plant form, it was allowed to stand there for about 30 seconds and then returned to a cage. When a rat was unable to climb up to the platform within a measuring time of 90 seconds, the rat was taken out from water, transferred onto the platform, allowed to stand there for about 30 seconds and returned to the cage. Incidentally, the escape latency at that time was counted as 90 seconds. Interval between trials was made about 30 minutes, four trials were conducted a day and they were defined as one session. Such a session was conducted for continued four days and (1) escape latency and (2) successful times (times of being able to reach the platform during four trials) were evaluated.

Results:

(1) Escape Latency

Result of the escape latency is shown in Table 2.

TABLE 2

| Group names | Case numbers | Escape latency (seconds) Sessions | | | |
|---|---|---|---|---|---|
| | | 1 | 2 | 3 | 4 |
| Normal group | 18 | 61.1 ± 4.3 | 31.2 ± 3.7 | 24.3 ± 3.2 | 16.3 ± 1.7 |
| Control group | 20 | 66.0 ± 3.4 | 54.9 ± 4.3 | 52.5 ± 5.9 | 54.3 ± 5.8 |
| 1 mg/kg group | 22 | 68.2 ± 3.5 | 61.8 ± 4.4 | 52.5 ± 6.9 | 46.9 ± 7.6 |
| 3 mg/kg group | 22 | 63.2 ± 3.8 | 48.7 ± 5.5 | 42.8 ± 6.4 | 34.9 ± 5.7 |
| 10 mg/kg group | 20 | 66.8 ± 3.7 | 44.5 ± 4.5 | 41.4 ± 5.2 | 31.2 ± 6.2 |

In the control group which was subjected to a 4VO treatment, the escape latency significantly became longer in second, third and fourth sessions as compared with the normal group (Second, third and fourth sessions: $p<0.001$: Wilcoxon's rank sum test).

In the groups of 3 mg/kg and 10 mg/kg (2R)-2-propyloctanoic acid, escape latency was significantly short in the fourth session as compared with the control group ($p<0.05$: Wilcoxon's rank sum test).

(2) Successful Times

Rate of rat numbers in successful times was calculated and the result is shown in the following Table 3.

TABLE 3

| Group names | Case numbers | Successful times | Escape latency (seconds) Sessions | | | |
|---|---|---|---|---|---|---|
| | | | 1 | 2 | 3 | 4 |
| Normal group | 18 | 0 | 0.0 | 0.0 | 0.0 | 0.0 |
| | | 1 | 27.8 | 0.0 | 0.0 | 0.0 |
| | | 2 | 33.3 | 5.6 | 5.6 | 0.0 |
| | | 3 | 33.3 | 44.4 | 11.1 | 11.1 |
| | | 4 | 5.6 | 50.0 | 83.3 | 88.9 |
| Control group | 20 | 0 | 15.0 | 5.0 | 10.0 | 5.0 |
| | | 1 | 25.0 | 20.0 | 25.0 | 30.0 |
| | | 2 | 35.0 | 30.0 | 10.0 | 20.0 |
| | | 3 | 20.0 | 35.0 | 20.0 | 25.0 |
| | | 4 | 5.0 | 10.0 | 35.0 | 20.0 |
| 1 mg/kg group | 22 | 0 | 22.7 | 9.1 | 22.7 | 18.2 |
| | | 1 | 27.3 | 22.7 | 22.7 | 22.7 |
| | | 2 | 31.8 | 31.8 | 0.0 | 4.5 |
| | | 3 | 13.8 | 27.3 | 4.5 | 9.1 |
| | | 4 | 4.5 | 9.1 | 50.0 | 45.5 |
| 3 mg/kg group | 22 | 0 | 18.2 | 9.1 | 13.6 | 45.5 |
| | | 1 | 18.2 | 13.6 | 4.5 | 4.5 |
| | | 2 | 40.9 | 9.1 | 22.7 | 0.0 |
| | | 3 | 13.6 | 27.3 | 9.1 | 31.8 |
| | | 4 | 9.1 | 40.9 | 50.0 | 54.5 |
| 10 mg/kg group | 20 | 0 | 15.0 | 0.0 | 0.0 | 0.0 |
| | | 1 | 35.0 | 15.0 | 15.0 | 5.0 |
| | | 2 | 5.0 | 10.0 | 10.0 | 10.0 |
| | | 3 | 35.0 | 50.0 | 40.0 | 15.0 |
| | | 4 | 10.0 | 25.0 | 35.0 | 70.0 |

In the second, third fourth sessions, the control group shows significant difference as compared with the normal group (second and third sessions: $p<0.05$: $\chi^2$ test; fourth session: $p<0.001$: $\chi^2$ test).

In the groups of 3 mg/kg and 10 mg/kg (2R)-2-propyloctanoic acid, escape latency showed significant difference in the fourth session as compared with the control group ($p<0.05$: $\chi^2$ test).

1-B-3: Evaluation by a Histological Observation

On the next day of completion of the water maze learning test, pentobarbital (about 35 mg/kg, Nembutal (registered trade mark) Injection; manufactured by Dainippon Pharmaceutical) was intraperitoneally administered to the rat to anesthetize. After that, brain was perfused transcardially with a heparin-added (10 U/mL, heparin sodium injection solution; manufactured by Shimizu Seiyaku) physiologically saline solution (Physisalz-PL, manufactured by Fuso Yakuhin Kogyo) and then brain was perfused and fixed with a 10% neutral buffered formalin (manufactured by Wako Pure Chemical). Whole brain was excised and preserved in a 10% neutral buffered formalin and, after that, specimens for histopathological test were prepared.

With regard to the specimens for histopathological test, three kinds of specimens, i.e. (1) Nissl-stained specimen (a site of 5.7 mm from interaural line), (2) specimen stained with hematoxylin-eosin and (3) unstained specimen (thickness: 10 µm) were prepared for brain tissue sample from one animal. Among them, with regard to the Nissl-stained specimen, right and left hippocampus CA1 nerve cell layer lengths and nerve cell numbers were measured by using Image Analyzer (MCID Elite 7.0 Rev.1.0) and numbers per unit length (mm) were calculated to conduct a histological evaluation.

Result:

Result of measurement of nerve cell numbers in the hippocampus CA1 region is shown in the following Table 4.

TABLE 4

| Groups names | Case numbers | Nerve cell density (cells/mm) | p value |
|---|---|---|---|
| Normal group | 18 | 129.9 ± 3.3 | — |
| Control group | 20 | 43.6 ± 6.2 | <0.0001 |
| 1 mg/kg group | 22 | 45.0 ± 5.6 | 0.7818 |
| 3 mg/kg group | 22 | 61.0 ± 4.8 | 0.0495 |
| 10 mg/kg group | 20 | 71.4 ± 5.5 | 0.0015 |

A significant decrease in nerve cell numbers was noted in the control group as compared with the normal group (p<0.001: Wilcoxon's rank sum test).

In the groups of 3 mg/kg and 10 mg/kg (2R)-2-propyloctanoic acid, nerve cell numbers significantly increased as compared with the control group (3 mg/kg: p<0.05: Wilcoxon's rank sum test; 19 mg/kg: p<0.01: Wilcoxon's rank sum test).

Example 2

Investigation of Effect on In Vitro Nerve Stem Cell Differentiation:
2-A: Evaluation by Differentiation Test of Stem Cells Derived from Fetal Brain of Rats
2-A-1: Preparation of Samples and Evaluation of Nerve Cell Numbers Fetus was taken out from a pregnant rat of Wistar strain and striatum was excised from brain of the fetus. Cells were dispersed by means of pipetting and incubated for six to seven days in a growth medium (a DMEM/F12 medium (manufactured by Gibco) containing N2 additive (N2 Plus Supplement; R&D Systems), antibiotics, basic fibroblast growth factor (20 ng/mL bFGF; manufactured by R&D Systems) and epithelial cell growth factor (20 ng/mL EGF; manufactured by R&D Systems). The resulting neurospheres were recovered, cells were dispersed by means of pipetting and culturing was conducted for six to seven days more using a growth medium. Neurospheres which were produced again were recovered and, after cells were dispersed, they were cultured on a chamber slide subjected to a poly-L-ornithine coating. After incubating for 24 hours, exchange to a differentiated medium comprising a test compound (a DMEM/F12 medium comprising N2 additive, antibiotic and 1% fetal bovine serum) was conducted. After differentiating for seven days, fixation was conducted with 4% paraformaldehyde and a immunostaining was conducted using a mouse anti-βIII-tubulin antibody (second antibody: FITC-labeled anti-mouse IgG antibody) which is to be an index for differentiation from nerve stem cells to nerve cells).

Figure 2:
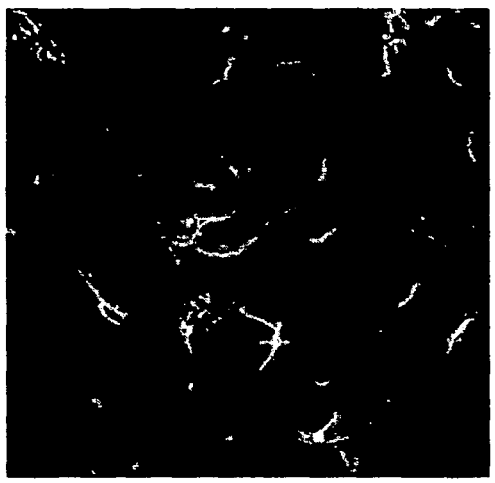
FIG. 2 shows pictures under microscope which show the changes in βIII-tubulin-positive cell numbers in a stem cell differentiation test derived from brain of fetus of rat incubated for 7 days in a DMEM/F12 medium comprising 1% fetal bovine serum (manufactured by Dainippon Pharmaceutical) (no compound-added group) and in a medium comprising (2R)-2-propyloctanoic acid (compound-added group).
Figure 2:
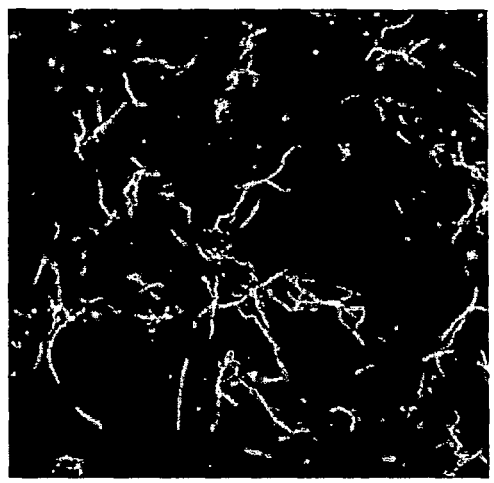

Result:

Nerve stem cells derived from striatum of a rat were incubated for seven days in a DMEM/F12 medium comprising 1% fetal bovine serum (Dainippon Pharmaceutical) (no compound-added group) or in a medium comprising a test compound (compound-added group) and, as a result, βIII-tubulin-positive (Tuj1$^+$) cell numbers per visual field under a microscope (100 magnifications) significantly increased in the group to which the compound was added as compared with the no compound-added group. For example, when 30 µmol/L of (2R)-2-propyloctanoic acid was used, the cell numbers in the no compound-added group were 8±1.3 (in eight visual fields) while those in the group to which the compound was added were 31±4.6 (in eight visual fields). The result is shown in FIG. 2.

2-A-2: Confirmation of Differentiating Stage of Nerve Cells

With regard to the above nerve cells prepared by differentiation of nerve stem cells derived from striatum of rats, their differentiation stage was confirmed by means of immunostaining. Incidentally, for the confirmation of mature nerve cells, anti-MAP2 antibody was used while, for the confirmation of functional nerve cells, anti-GABA antibody was used.

Result:

The result of counting of positive cell numbers per visual field stained using an anti-MAP2 antibody was that, in no compound-added group, they were 34±0.9 while, in a group to which 30 µmol/L of (2R)-2-propyloctanoic acid was added, they were 50±7.4.

The result of counting of positive cell numbers per visual field stained using an anti-GABA antibody was that, in no compound-added group, they were 19±2.7 while, in a group to which 30 µmol/L of (2R)-2-propyloctanoic acid was added, they were 101±9.5.

From the above results, it was found that mature nerve cells and functional nerve cells were prepared when nerve stem cells derived from striatum of fetus of rat were differentiated into nerve cells using a medium to which (2R)-2-propyloctanoic acid was added.

Example 3

Investigation of Effect on Differentiation from Primary-Culture Astrocytes to Nerve Cells:
3-A: Evaluation by Differentiation Test of Astrocytes Derived from Cerebral Cortex of Rats
3-A-1: Preparation of Samples Cerebrum was excised from newly-born rats of Wistar strain and, after removal of meninx under a stereoscopic microscope, it was ground with a frost part of a slide glass with frost in an ice-cooled DMEM medium to prepare a suspension. Centrifugal separation was conducted at 100×g for 3 minutes and the precipitate was suspended in a 10% bovine fetal serum-DMEM medium and sown in a 75-cm$^2$ flask. After two days from the start of culturing, cell purification was conducted.

On the 19th day from the start of the culturing, astrocytes were recovered using 0.05% trypsin/EDTA and the cells were suspended again using a differentiation medium (a DMEM/F12 medium (Gibco) containing N2 additive (N2 Plus Supplement; R&D Systems) and 1% fetal bovine serum (manufactured by Dainippon Pharmaceutical). That was sown on a chamber slide and, on the next day, the culturing solution was exchanged to a differentiated medium (a DMEM/F12 medium comprising N2 additive, antibiotic and 1% fetal bovine serum) containing a test compound. After differentiating for seven days, fixation was conducted using 4% paraformaldehyde and the following immunostaining was conducted.

3-A-2: Confirmation of Differentiation Stage of Nerve Cells

With regard to nerve cells prepared by differentiation of astrocytes derived from cerebral cortex of rats, their differentiation stage was confirmed by means of immunostaining. Incidentally, anti-βIII-tubulin antibody and anti-doublecortin antibody were used for confirmation of young nerve cells; anti-MAP2 antibody, anti-NeuN antibody and anti-NSE antibody were used for confirmation of mature nerve cells; and anti-GABA antibody was used for confirmation of functional nerve cells.

Result:

As a result of counting of positive cell numbers per visual field stained by an anti-βIII-tubulin antibody, they were 93±10.9 in no, compound-added group, 177±11.8 in a group to which 30 μmol/L of (2R)-2-propyloctanoic acid was added, 230±11.0 in a group to which 100 μmol/L of (2R)-2-propyloctanoic acid was added and 174.8±7.8 in a group to which 300 μmol/L of 2-propylpentanoic acid was added.

As a result of counting of positive cell numbers stained by an anti-doublecortin antibody, they were 55±5.7 in no compound-added group and 168±16.6 in a group to which 30 μmol/L of (2R)-2-propyloctanoic acid was added.

As a result of counting of positive cell numbers stained by an anti-MAP2 antibody, they were 50±7.4 in no compound-added group and 104±10.3 in a group to which 30 μmol/L of (2R)-2-propyloctanoic acid was added.

As a result of counting of positive cell numbers stained by an anti-NeuN antibody, they were 106 in no compound-added group and 199 in a group to which 30 μmol/L of (2R)-2-propyloctanoic acid was added.

As a result of counting of positive cell numbers stained by an anti-NSE antibody, they were 108 in no compound-added group and 166 in a group to which 30 μmol/L of (2R)-2-propyloctanoic acid was added.

As a result of counting of positive cell numbers stained by an anti-GABA antibody, they were 20±1.0 in no compound-added group and 60±8.8 in a group to which 30 μmol/L of (2R)-2-propyloctanoic acid was added.

From the above results, it was found that matured nerve cells and functional nerve cells were obtained when astrocytes derived from cerebral cortex of rats were differentiated into nerve cells using a medium to which (2R)-2-propyloctanoic acid was added.

Preparation Example 1

(2R)-2-Propyloctanoic acid (2.0 kg) and trisodium phosphate dodecahydrate (3.54 kg) were added and made into 40 L using water for injection. After making it into a uniform solution, it was filtered through an aseptic filter (Durapore 0.22 μm membrane), each 2 mL thereof was filled in an ampoule and subjected to a high-pressure steam sterilization (at 123° C. for 15 minutes) to give 20,000 ampoules each containing 100 mg of active ingredient.

INDUSTRIAL APPLICABILITY

Since the compound of the present invention has a accelerating action for nerve regeneration in animals including humans or particularly in humans, it is useful for prevention and/or treatment of neurodegenerative diseases, and therefore it can be utilized as pharmaceuticals. Moreover, when it is used as an additive for culturing in the preparation of nerve cells for transplant in vitro, nerve cells can be efficiently prepared, and therefore, it can be utilized for preparation of cells having pharmaceutical uses.

The invention claimed is:

1. A method of in vitro culturing astrocytes for inducing differentiation into neurons, comprising the steps of:
   preparing astrocytes from a mammal,
   in vitro culturing said astrocytes in differentiation medium comprising N2 supplement, and
   in vitro culturing said astrocytes in media comprising (2R)-2-propyloctanoic acid or a salt thereof,
   wherein said culturing in said media induces the proliferation and differentiation of said astrocytes into neurons.

2. The method according to claim 1, wherein the effective amount of (2R)-2-propyloctanoic acid or a salt thereof is about 30 μM.

* * * * *